United States Patent [19]
Centkowski et al.

[11] Patent Number: 4,862,199
[45] Date of Patent: Aug. 29, 1989

[54] ADJUSTABLE ADAPTER FOR BORESCOPE AND FILM/VIDEO CAMERA

[75] Inventors: Mark Centkowski, Santa Monica; Steven E. Manios, Sr., Northridge, both of Calif.; James Weaver, Glaewyne, Pa.

[73] Assignee: Innovision Optics, Inc., Santa Monica, Calif.

[21] Appl. No.: 241,715

[22] Filed: Sep. 8, 1988

[51] Int. Cl.$^4$ ............................................. G03B 29/00
[52] U.S. Cl. ....................................... 354/62; 354/195.1
[58] Field of Search ............................... 354/62, 195.1

[56] References Cited

U.S. PATENT DOCUMENTS

| | | | |
|---|---|---|---|
| 3,257,902 | 6/1966 | Hopkins | 88/57 |
| 4,063,263 | 12/1977 | Krewalk, Sr. | 354/253 |
| 4,196,990 | 4/1980 | Forsyth | 354/62 |
| 4,264,167 | 4/1981 | Plummer | 354/62 |
| 4,273,431 | 6/1981 | Farmer et al. | 354/59 |
| 4,413,278 | 11/1983 | Feinbloom | 354/93 |
| 4,611,888 | 9/1986 | Prenovitz et al. | 350/96.22 |
| 4,628,207 | 12/1986 | Elfert et al. | 250/461.1 |
| 4,655,569 | 4/1987 | Sims | 354/62 |
| 4,672,437 | 6/1987 | Casper | 358/101 |
| 4,676,593 | 6/1987 | Adachi et al. | 350/96.26 |
| 4,685,450 | 8/1987 | Collins et al. | 128/4 |
| 4,732,450 | 3/1988 | Lee | 350/96.18 |

Primary Examiner—Michael L. Gellner
Attorney, Agent, or Firm—Kelly, Bauersfeld & lowry

[57] ABSTRACT

An improved adapter is provided for joining an optical scope, such as a borescope, endoscope or the like, to a film or video camera. The adapter includes a multi-element relay lens assembly which directs real images viewed by the attached optical scope to the camera for filming. The multi-element relay lens assembly is longitudinally positionable within the adapter to provide a focusing control. A filter slot is further included within the adapter to allow for the insertion of an optical filter between the borescope and the camera without uncoupling either attachment from the adapter. In order to achieve improved image resolution at the camera aperture of images detected by the borescope, a scope's eyepiece optics and the camera lens are removed prior to coupling the borescope and the camera to the adapter. The adapter is capable of use with virtually all sizes and types of cameras and optical scopes, and attachment of the adapter to the camera and the borescope is effected in a manner allowing for selective rotational orientation of each element with respect to the other.

23 Claims, 4 Drawing Sheets

ADJUSTABLE ADAPTER FOR BORESCOPE AND FILM/VIDEO CAMERA

BACKGROUND OF THE INVENTION

This invention relates generally to optical couplers. More particularly, this invention relates to an adjustable adapter for coupling a film or video camera to an optical viewing device such as an endoscope, borescope or the like, so that images viewed by the optical scope can be filmed or photographed.

Previous devices for coupling a camera with an endoscope, arthroscope, borescope or similar viewing apparatus have been subject to commonly encountered problems which have limited their effectiveness. For example, when the coupled borescope and camera arrangement is used in a liquid (moist) environment, prior couplers commonly are unable to prevent minute liquid quantities from seeping in between the borescope eyepiece and the coupler. This liquid becomes entrapped and tends to fog the optics of the coupled arrangement.

Another common problem found in prior couplers or adapters arises when the optical scope is rotated relative to the coupler in order to vary the orientation of the optical scope with respect to the camera. In this instance, a coupling ring associated with the adapter, which engages the scope eyepiece, tends to bind up or present varied resistance during rotation, instead of providing a smooth and steady rotational adjustment.

Exemplary attempts to provide improved coupling devices or adapters are illustrated in U.S. Pat. Nos. 4,611,888; 4,413,278 and 4,264,16. Such coupling devices have been found to include several key limitations which thus far have not been effectively eliminated. One of these shortcomings arises because it is standard practice to use an adapter to couple an optical scope to a camera without first removing the scope's eyepiece optics. The disadvantage of coupling with the scope's eyepiece optics stems from the fact that the eyepiece optics provide a virtual image to the attached camera rather than the real image. The eyepiece optics are designed for visual use by a human eye which can generally resolve only about 8 to 10 lines/mm. While such a virtual image is acceptable for this low level of resolution, such is considered unacceptable for photography with modern cameras. A virtual image from the scope's eyepiece optics does not allow the user to achieve the high resolution benefits which a camera could provide if it received the real image from the optical scope (by bypassing the eyepiece optics), rather than the virtual image. In contrast to the 8 to 10 lines/mm ordinarily resolved by a human eye, a video camera can resolve between 40 and 60 line pairs/mm and, depending on the type of film, and a film camera can provide an even higher level of resolution. Thus, a coupling limitation exists in prior devices whereby the camera cannot achieve a desired high resolution level because of optical degradation and light loss occurring in the image as it passes through the optical scope's eyepiece optics.

Another limitation common in prior coupling devices is that a user of the coupled arrangement is unable to insert an auxiliary lens between the optical scope and the camera while they remain coupled together. An adapter which facilitates the use of auxiliary lenses or filters in a quick and easy fashion is essential when it is necessary to produce films or photographs having certain special effects. Prior adapters which contain no provision for auxiliary lens usage require uncoupling of the borescope or camera from the adapter so that shutter attachments or the like, providing auxiliary lenses, can be inserted between the camera and the optical scope. Often, when the photographer is trying to capture a rapidly changing microscopic image using a borescope, there is not enough time available for such uncoupling to allow for the attachment and detachment of auxiliary shutters or lens devices as needed.

Yet another constraint on the effectiveness of prior coupling adapters can be found in devices which utilize a relay lens to direct the image viewed by the optical scope to the camera lens. A relay lens is sometimes provided which consists of a single optical piece or in which the relay lens is not adjustably positionable in a manner providing focus control. In either of these arrangements, optimum optical efficiency is not possible. Greater efficiency in a relay lens arrangement can be obtained if the adapter utilizes a relay lens having multiple optical pieces for improved enlargement of a relayed image to a size appropriate for the camera. Optical efficiency and image quality can be further improved if the adapter can be provided with an adjustably positionable, multi-element relay lens assembly which allows for enhanced focusing control.

There exists, therefore, a significant need for a coupling adapter which can be utilized with an optical scope having its eyepiece optics removed, thus allowing the attached camera to receive an improved image having a high degree of resolution. Additionally, an improved adapter is needed which can provide selective orientation of the optical scope relative to the camera, which allows for the utilization of auxiliary lenses without requiring uncoupling or additional attachments, and which provides improved focusing control, optical efficiency and image quality through the use of an adjustably positionable, multi-element relay lens. Moreover, an improvement is needed wherein a borescope or the like, and a camera are coupled together in a manner facilitating detection of a real image by the camera directly at the camera aperture. The present invention fulfills these needs and provides further related advantages.

SUMMARY OF THE INVENTION

In accordance with the invention, an adapter is provided for quick and easy coupling of an optical scope such as an endoscope, borescope or the like, to a film or video camera. The adapter is attached to an optical scope in a manner wherein the eyepiece optics of the scope are removed prior to connection of the optical scope to the adapter. Removal of the eyepiece optics advantageously enables the adapter to relay images viewed by the optical scope to an attached camera in a manner providing high image resolution and improved optical efficiency. The adapter beneficially utilizes an adjustably positionable, multi-element relay lens which improves the optical quality of images relayed from the optical scope to the attached camera. Further, the adapter of the present invention provides for insertion and use of an auxiliary lens or optical filter between the scope and the camera while remaining coupled together via the adapter. Moreover the improved adapter is designed for compatibility with virtually all sizes and types of cameras and optical scopes, and provides for selective orientation of the optical scope with respect to the attached camera.

In accordance with a preferred form of the invention, the improved adapter includes a housing of generally circular cross section, having a mounting disk at one end for the attachment of a borescope or the like, and a coupling ring at the opposite end for the attachment of a film or video camera. A multi-element relay lens assembly is situated within the adapter housing for directing images viewed by the optical scope to the aperture of the camera. The multi-element relay lens assembly uses at least two optical pieces, and is constructed so that the longitudinal location of the relay lens assembly within the housing can be selectively fixed. In this regard, the adapter has a focus control ring surrounding a portion of the outer surface of the adapter housing for adjusting the longitudinal positioning of the relay lens within the housing. The provision of a plurality of selectively positionable optical pieces within the adapter housing results in more effective enlargement of a microscopic image obtained through the optical scope, to a size which is appropriate for the camera.

The adapter is specially configured to facilitate the insertion of an auxiliary lens or optical filter between the optical scope and the attached camera. A generally semi-circular filter slot is provided within the adapter housing for allowing auxiliary optical pieces to be inserted without requiring the optical scope or camera to be detached from the adapter. This allows for quick and easy use of a special effects lens or filter while avoiding the loss of time and missed opportunities which can occur in prior adapters.

The mounting disk at a first end of the adapter housing attaches to a borescope or the like, in a manner which permits heightened optical quality of films or photographs taken by the camera. More particularly, such heightened optical quality is achieved, in part, by removing the scope's eyepiece optics prior to coupling the scope to the adapter. The omission of the optical scope's eyepiece optics is significant because if the eyepiece optics are left in place, the real image viewed by the optical scope will be subject to light loss and optical degradation while passing through the eyepiece optics en route to the attached camera. As a result, the degree of resolution normally achievable by the camera will be lowered because the camera is resolving a virtual image of lesser optical quality than the original real image. In the coupled borescope and camera arrangement of the present invention, the real image is not subject to optical degradation and thus higher resolution is achieved. The mounting disk is designed for compatibility with virtually all types and sizes of optical scopes and is secured to the adapter housing by a universal mounting ring.

The adapter connects to the camera by use of a camera coupling ring, directly adjacent to the camera aperture following removal of the camera lens. A variety of coupling rings are provided for compatibility with virtually all camera types and sizes. Both the coupling ring and the scope mounting disk are designed to allow for selective rotational orientation of the optical scope with respect to the camera. The mounting disk provides a pilot pin which is selectively aligned with any selected one of a plurality of holes provided in the adapter housing. At the opposite end of the adapter housing, another pilot pin projects outwardly from the housing for selective alignment with any one of a plurality of small apertures which are commonly provided around the front, lens-receiving portion of a camera. In either case, alignment and engagement of the pilot pin with a selected hole or aperture will fix the rotational orientation of the optical scope relative to the camera.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 3:
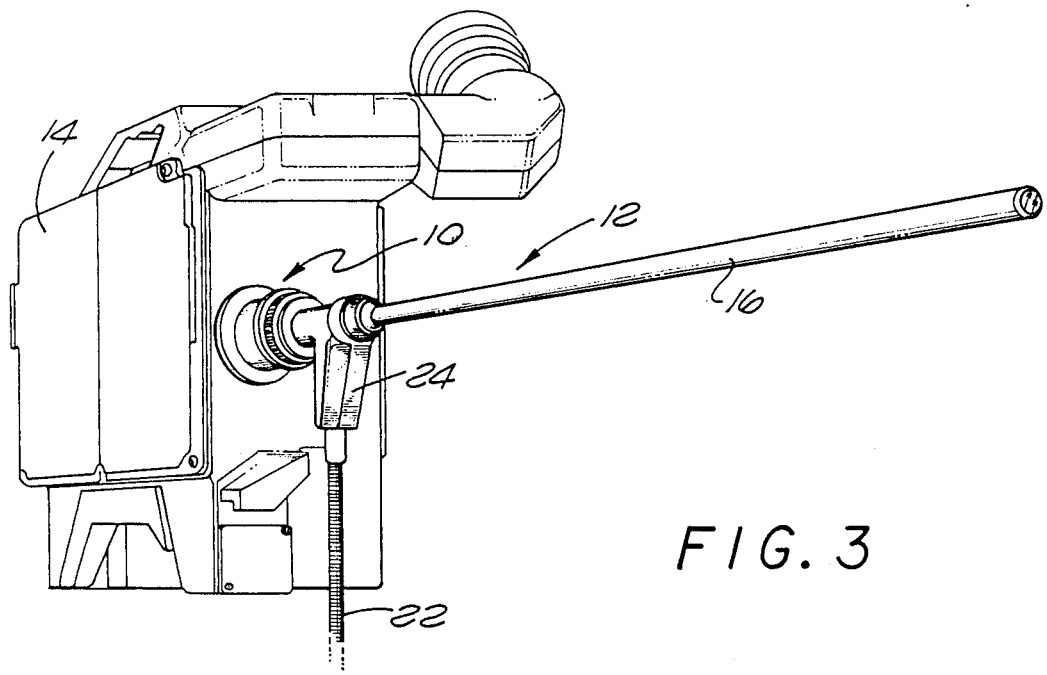
FIG. 3 is a perspective view of the novel coupled arrangement using an improved adapter to connect the borescope with a video camera.

As shown in the drawings for purposes of illustration, the present invention resides in an improved adapter, generally designated in the accompanying drawings by the reference number 10, for coupling an optical scope, such as a borescope 12, endoscope, or the like, to a film or video camera 14, and in the resultant coupled arrangement. The coupled arrangement of a video camera 14 and a borescope 12 as shown in FIG. 3, allows real microscopic images viewed by the borescope to be relayed via the coupling adapter 10 for filming by the attached camera.

Figure 1:
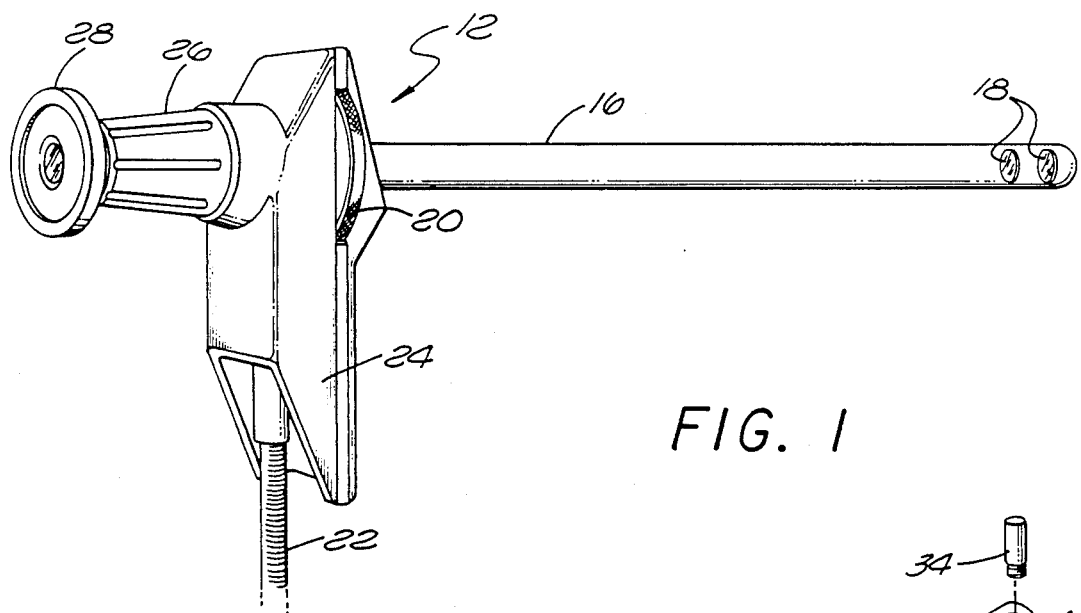
FIG. 1 is a perspective view of a borescope having its eyepiece cup and eyepiece optics in place for viewing virtual by the human eye.

A typical optical scope or borescope 12, which is to be coupled with the coupling adapter 10, is illustrated in FIG. 1. Such borescopes 12 are characterized by their distinctive long narrow lens barrel 16 which is made of a durable material such as chrome oxide plated stainless steel. Housed within the lens barrel 16 are optical scope lenses 18 which can be laser-cut polished glass pieces. The borescope 12 also includes a rotation control disk 20 which provides for limited rotation of the lens barrel 16. The light for the optical scope lenses 18 is provided by the scope's own daylight color temperature source which is transmitted through built-in fiber optic bundles. A light guide cable 22 connects the borescope 12 to the light source through a handle 24. A scope focusing barrel 26 and an eyepiece cup 28 are threaded onto the handle 24 and contain the scope eyepiece optics 30.

Figure 2:
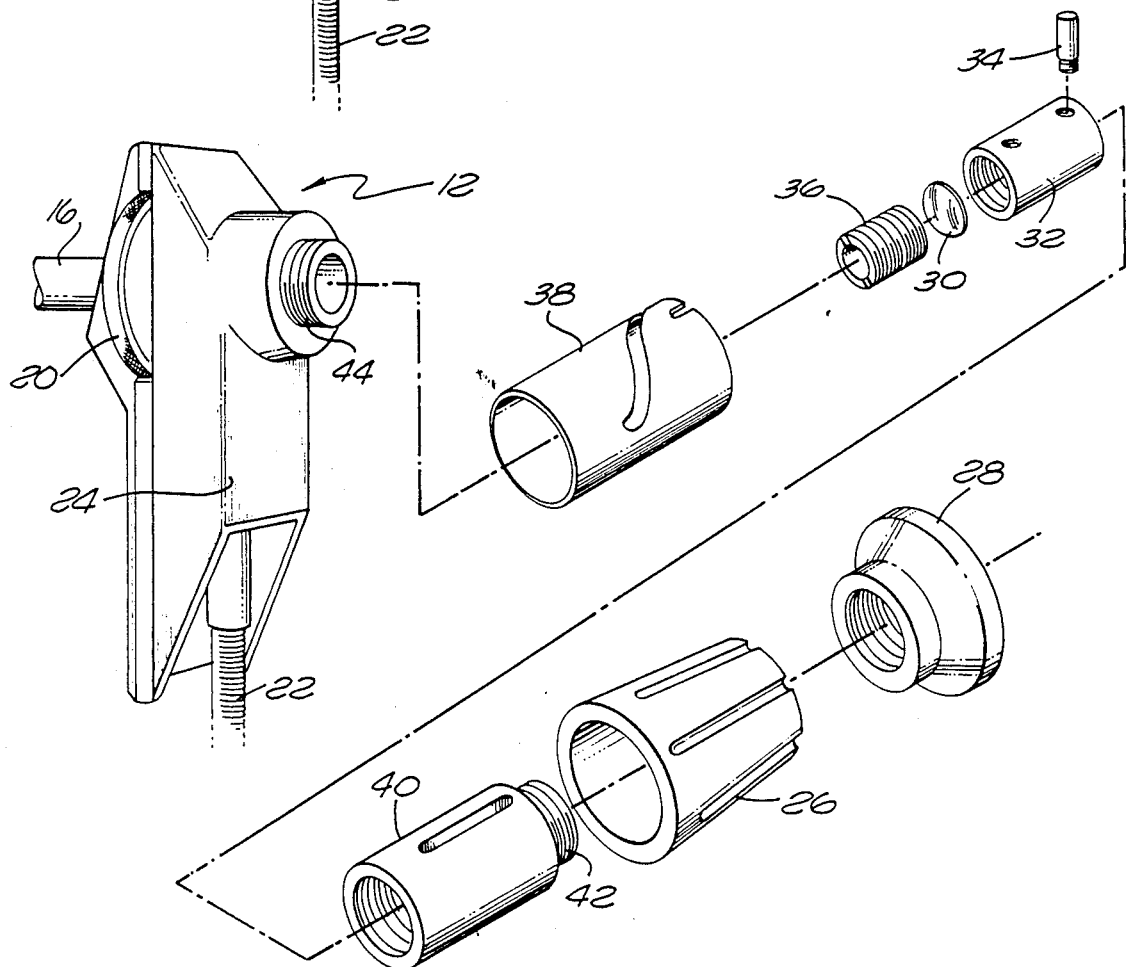
FIG. 2 is an exploded perspective view of exemplary eyepiece components, which are removed from the borescope so that the inventive coupled arrangement can be made.

When the optical borescope 12 is joined by the inventive coupling adapter 10 to the camera 14, the coupled borescope and camera are capable of providing photography of a higher resolution than that achievable with previous coupled arrangements, because a feature of the present invention lies in the removal of the scope's eyepiece optics 30 prior to connection of the borescope with the coupling adapter. Removal of the borescope's eyepiece optics 30 involves detachment of all of the eyepiece elements illustrated in FIG. 2. The borescope's eyepiece optics or lens 30 is usually contained within a lens casing 32 which utilizes a set screw 34 and a connector 36 to secure the eyepiece optics in place. This structure, along with a movable casing 38 and an eyepeice housing 40, fit within the focusing barrel 26.

Prior coupling adapters are typically connected to the optical scope 12 by removing the eyepiece cup 28 and then threading the coupling adapter onto the eyepiece housing threads 42. The result is a coupled arrangement in which the scope's eyepiece optics 30 are left in place within the eyepiece housing 40. In contrast, the coupling arrangement of the present invention removes the scope's eyepiece optics 30 as well as the eyepiece cup 28, so that the coupling adapter 10 is threaded onto the scope threads 44 rather than the eyepiece housing threads 42. This advantageously prevents optical degradation of an image as it travels from the optical scope 12, through the adapter 10 and to the camera 14, by avoiding optical distortion which commonly occurs if the image is filmed through the scope's eyepiece optics 30.

The adapter 10 of the present invention advantageously provides for the insertion and utilization of an auxiliary lens or optical filter 46 between the camera 14 and the borescope 12 while the camera and the borescope remain coupled together. Additionally, several improvements have been made in the relay lens assembly 48 of the adapter 10, which is located within an adapter housing 50, to direct real images viewed by the optical scope 12 back to the camera 14. One improvement involves the use of an adjustably positionable, multi-element relay lens assembly 48 which utilizes a plurality of optical pieces 52. Prior adapters commonly included a relay lens which contained only one or two optical pieces which were not movable in a manner providing for selective longitudinal positioning of the relay lens assembly within the adapter housing. Another improvement in the relay lens assembly 48 of the adapter 10 is that the relay lens assembly is situated to focus the relayed image at the aperture of an attached camera rather than at the auto focal plane of the camera. Further advantages of the adapter 10 are that it provides for selective orientation of the optical scope 12 with respect to the camera 14, it is lightweight and easy to use, and it is adaptable for virtually all types and sizes of cameras and optical scopes.

Figure 4:
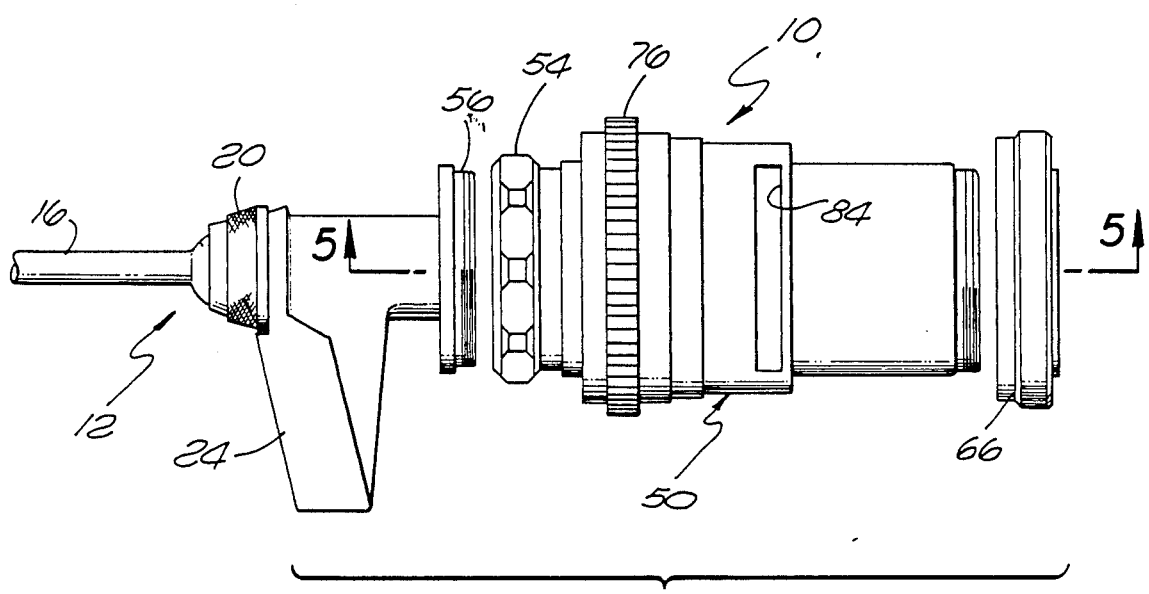
FIG. 4 is an exploded elevational view of the coupling adapter of the present invention, and its relationship with the exemplary borescope.
Figure 5:
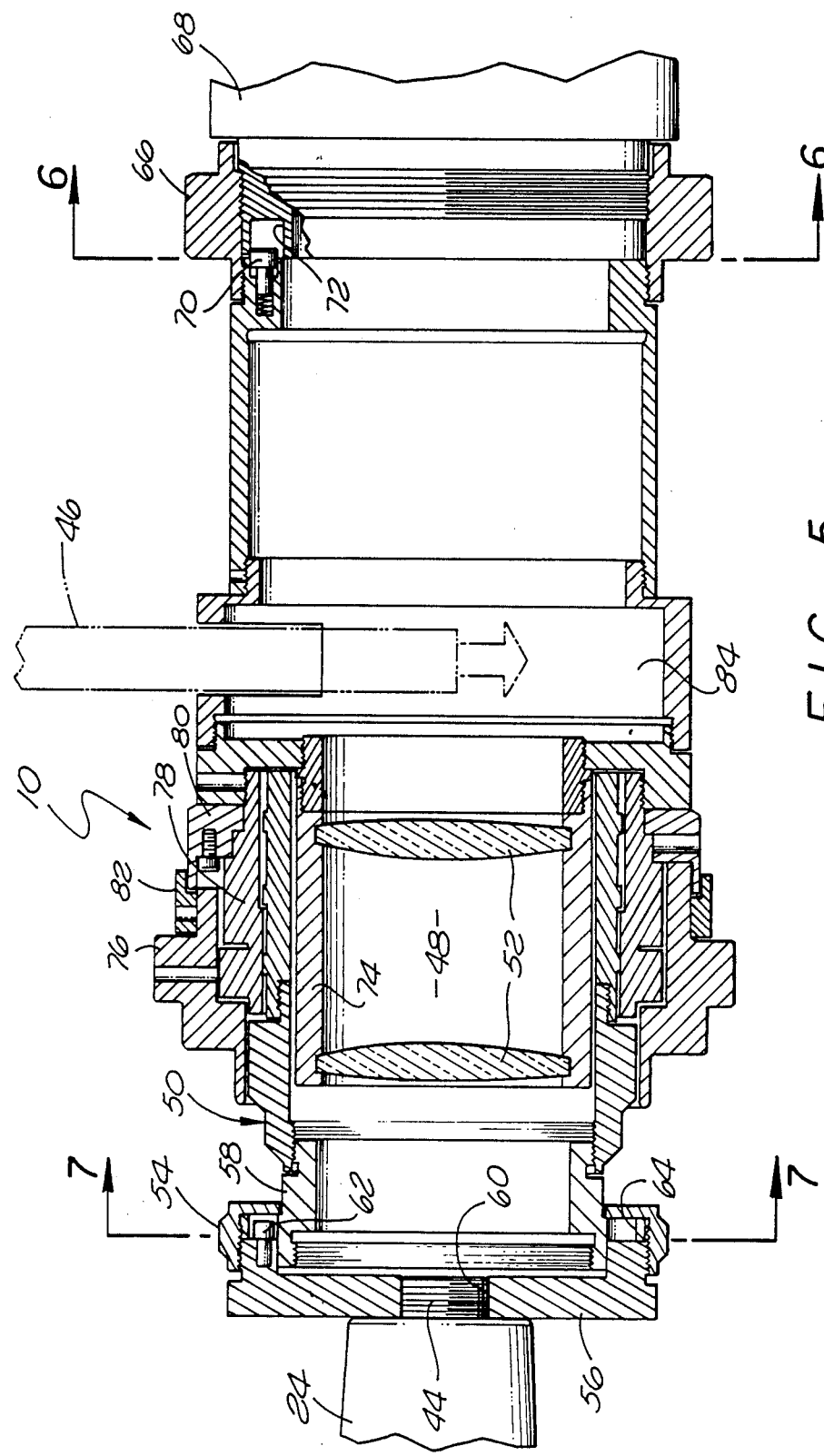
FIG. 5 is a fragmented, enlarged, sectional view taken generally along line 5—5 of FIG. 4, illustrating the particular construction and features of the improved

In accordance with the present invention, and with reference to FIGS. 4 and 5, the adapter 10 includes a tubular-type adapter housing 50 having a generally circular cross-section. At one end of the adapter housing 50 is a universal locking ring 54 which is used to secure an optical scope mounting disk 56 to the adapter 10. A "T" mount 58 retains the locking ring 54 on the adapter housing 50. The optical scope mounting disk 56 contains a central aperture 60. The scope threads 44 are exposed by removal of the optical scope eyepiece cup 28, the eyepiece optics 30, and the focusing barrel 26 (see FIG. 2), and the scope mounting disk 56 is attached to the borescope 12 by screwing the scope threads 44 into the aperture 60 of the mounting disk. The scope mounting disk 56 also provides a pilot pin 62 which can be selectively aligned and engaged with any one of plurality of holes 64 provided about the periphery of the "T" mount 58, so that selective orientation of the optical scope 12 with respect to the camera 14 can be achieved. In addition, product information such as the manufacturer's serial number can be provided on the scope mounting disk 56.

Figure 6:
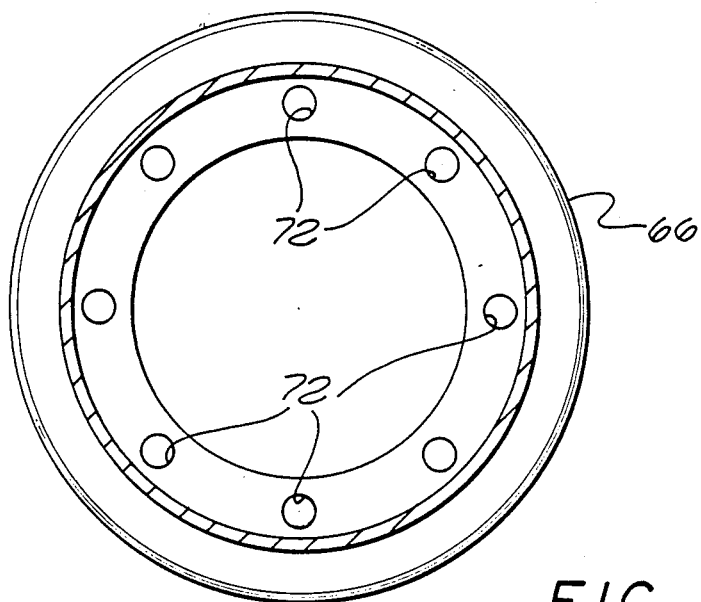
FIG. 6 is a sectional view taken generally along line 6—6 of FIG. 5, illustrating, among other things, a plurality of pilot-pin receiving small apertures spaced around the front face of the camera and the camera aperature.
Figure 7:
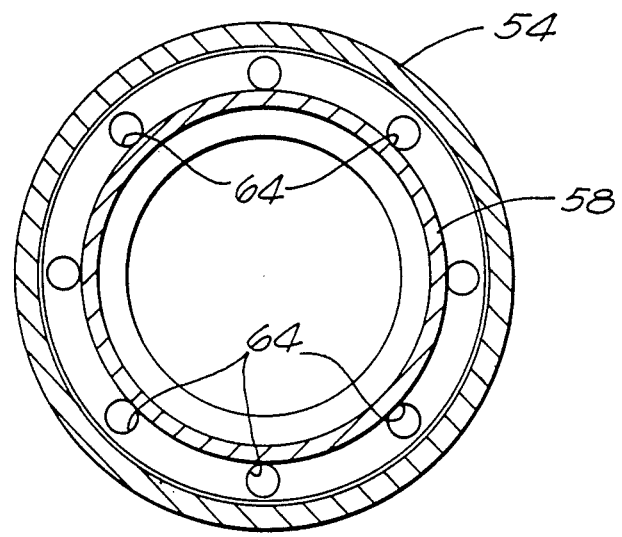
FIG. 7 is sectional view taken generally along line 7—7 of FIG. 5, illustrating, among other things, the end of the adapter housing with its mounting disk removed to expose a plurality of pilot-pin receiving holes provided around the housing end.

A similar arrangement at the opposite end of the adapter housing 50 promotes connection of the adapter 10 to the camera 14 in a manner which also provides for the selective orientation of the borescope 12 with respect to the camera. At this opposite or second end, the camera 14 is secured to the adapter housing 50 by a camera coupling ring 66 which is interiorly threaded to receive both the adapter housing 50 and a threaded camera stub 68. A second pilot pin 70 extends from the adapter housing 50 so that it can be selectively aligned and engaged with any one of a plurality of apertures 72 which are commonly provided about the camera stub 68 (see FIGS. 5 and 6). Both pilot pins 62 and 70 are preferably spring biased toward the adjacent mounting disk holes 64 or camera stub apertures 72.

Interchangeability of variously dimensioned camera coupling rings 66 is accommodated by configuring each camera coupling ring with a threaded end that matches the adapter housing 50, and an opposite end that is dimensioned to match a particular camera stub 68. Selective orientation of the borescope 12 with respect to the camera 14 is achieved by alignment and engagement of the camera pilot pin 70 with a selected aperture 72. To change the orientation of the borescope 12 with respect to the camera 14, the coupling ring 66 is unscrewed from the adapter housing 50, the pilot pin 70 is aligned with a different selected aperture 72, and then the coupling ring 66 is tightened back onto the housing 50. It should be noted that the connection between the camera coupling ring 66 and the camera stub 68 is made with the camera lens (not shown) removed. With the camera lens absent, images relayed by the adapter 10 from the optical scope 12 to the attached camera 14 will be focused at the aperture of the camera rather than the camera's auto focal plane.

The adapter 10 utilizes a multi-element relay lens assembly 48 which contains a plurality of optical pieces 52. The particular arrangement shown accurately and efficiently enlarges a microscopic image viewed by the optical scope 12 to a size which is more appropriate for the camera 14. As mentioned previously, prior to coupling the scope 12 and adapter 10, the optical scope's eyepiece optics 30 are removed. The image which is relayed by the relay lens assembly 48 is a real image rather than a virtual image. A virtual image results when the real image viewed by an optical scope 12 suffers light loss and optical degradation when it is passed through the optical scope eyepiece optics 30 for viewing by a human eye. This virtual image is of sufficient optical quality for a human eye, which can only resolve about 8 to 10 lines per millimeter. However, a virtual image is not of sufficient optical quality to allow an attached video camera 14 to achieve the 40 to 60 line pairs per millimeter of resolution which it would normally be capable of. The resolution limitations caused by using a virtual image are even more disadvantageous and pronounced when the attached camera is a film camera, which, depending on the type of film, is capable of a much higher degree of resolution than a video camera. For these reasons, the multi-element relay lens assembly 48 relays real images, rather than virtual images, back to the attached camera 14.

A relay lens housing 74 contains the optical pieces 52 and enables movement of the optical pieces as a unit. Focusing of the multi-element relay lens assembly 48 is achieved by selectively positioning the lens housing 74 within the adapter housing 50. This is accomplished by adjustment of a focusing ring 76 which surrounds a portion of the adapter housing 50. The inside barrel of the focus control ring 76 contains indentations (not shown) which provide a worm gear type engagement with a focusing ring mount 78. Rotation of the focus control ring 76 results in a change in the longitudinal positioning of the multi-element relay lens assembly 48 and its housing 74 within the adapter housing 50. A focus stop ring 80 limits rotation of the focus control ring 76 to 180 degrees. Adjacent to the focus control ring 76 is an index ring 82 which can contain markings to help a photographer align the focus control ring 76 in a desired position. The use of highly corrected glass optical pieces 52 is preferred, although optical pieces made of plastic or other suitable material could also be used in the present invention. adapter 10 provides an adjustable, longitudinally positionable, multi-element relay lens assembly 48, including a plurality of optical pieces 52 for improved optical efficiency. The adapter 10 is lightweight, easy to use, and is adaptable to virtually all types and sizes of cameras and optical scopes.

Although a particular embodiment of the invention has been described in detail for purposes of illustration, various modifications may be made without departing from the spirit and scope fo the invention. Accordingly, the invention is not to be limited, except as by the appended claims.

We claim:

1. An adapter for coupling a borescope or the like to a camera, comprising:
    an adapter housing having a first end and a second end;
    means for attaching the first end of the adapter housing to the borescope whereby a real image detected by the borescope is provided to the adapter;
    means for attaching the second end of the adapter housing to the camera whereby the real image is directed by the adapter to a camera aperture;
    a multi-element relay lens assembly within the housing having at least two optical pieces for directing the real image viewed by the borescope to the camera; and
    means for adjusting the longitudinal positioning of the relay lens assembly within the housing, the adjusting means providing a focus control for the relay lens assembly.

2. An adapter as set forth in claim 1, wherein the means for attaching the first end of the adapter housing to the borescope comprises a scope mounting disk having a threaded aperture for receiving a threaded end of the borescope, the threaded end of the borescope having been exposed by removal of borescope eyepiece optics, the scope mounting disk further having a threaded periphery and providing a pilot pin, wherein the mounting disk is secured to the adapter housing by threaded engagement of its periphery with a threaded locking ring located at the first end of the housing, the first end having a plurality of holes therein whereby selective orientation of the mounting disk and the borescope with respect to the adapter housing is achieved by alignment and engagement of the pilot pin with a selected one of the plurality of holes.

3. An adapter as set forth in claim 1, wherein the means for attaching the second end of the adapter housing to the camera comprises an interchangeable coupling ring having opposite threaded ends for threaded engagement with the second end of the adapter housing and with the camera, respectively.

4. An adapter as set forth in claim 3, wherein the second end of the adapter housing provides a pilot pin which can be selectively aligned with a plurality of small apertures provided about the camera aperture.

5. An adapter as set forth in claim 1, wherein the means for adjusting the longitudinal positioning of the relay lens assembly includes a rotatable focus control ring.

6. An adapter as set forth in claim 1, including a filter slot situated between the relay lens assembly and the second end, wherein auxiliary lenses or optical filters can be inserted within the adapter housing without uncoupling the borescope or the camera from the adapter.

7. An adapter as set forth in claim 6, wherein the filter slot is generally semi-circular.

8. A coupled borescope and camera assembly, comprising:
    a borescope having its eyepiece optics removed;
    a camera having its lens removed to expose a camera aperture; and
    an adapter for coupling the borescope and the camera together, the adapter including:
    an adapter housing;
    means for attaching the adapter housing to the borescope at a first end of the housing;
    means for attaching the adapter housing to the camera at a second end of the housing;
    optical means within the housing for directing real images viewed by the borescope to the camera; and
    means for focusing the optical means.

9. An assembly as set forth in claim 8, wherein the optical means includes a multi-element relay lens assembly having at least two optical pieces.

10. An assembly as set forth in claim 9, wherein the focusing means adjusts the longitudinal positioning of the multi-element relay lens assembly within the adapter housing.

11. An assembly as set forth in claim 8, including means for inserting an optical filter between the borescope and the camera.

12. An assembly as set forth in claim 11, wherein the means for inserting an optical filter allows for the insertion of an optical filter into the adapter while the borescope and the camera remain coupled together.

13. An assembly as set forth in claim 12, wherein the means for inserting an optical filter comprises a filter slot within the adapter housing.

14. An assembly as set forth in claim 13, wherein the filter slot is generally semi-circular.

15. An assembly as set forth in claim 8, wherein the adapter provides means for selectively orienting the borescope with respect to the camera.

16. An assembly as set forth in claim 15, wherein the means for attaching the adapter housing to the borescope comprises a scope mounting disk which includes a threaded aperture for receiving a threaded end of the borescope, the threaded end of the borescope having been exposed by removal of the eyepiece optics, the mounting disk having a threaded periphery and providing a pilot pin wherein the mounting disk is secured to the adapter housing by threaded engagement of its periphery with a threaded locking ring located at the first end of the adapter housing, the first end having a plurality of holes therein whereby selective orientation of the mounting disk and the borescope with respect to the adapter housing is achieved by alignment and engagement of the pilot pin with a selected one of the plurality of holes.

17. An assembly as set forth in claim 16, wherein the mounting disk is usable with a wide variety of sizes and types of optical scopes and wherein the pilot pin is spring biased.

18. An assembly as set forth in claim 15, wherein the means for attaching the adapter housing to the camera at the second end of the housing includes an interchangeable coupling ring having a threaded portion for engaging the second end of the adapter housing and the camera, wherein the second end of the adapter housing provides a pilot pin which can be selectively aligned with a plurality of small apertures provided about the camera aperture.

19. A method for coupling a borescope or the like to a camera, the steps comprising:
providing a borescope having its eyepiece optics removed so that a real image is detectable through the borescope;
providing a camera having its lens removed to expose a camera aperture;
coupling the borescope to a first end of an adapter having optical means for focusing the real image from the borescope through the adapter; and
coupling the camera to a second end of the adapter so that the real image can be focused through the adapter into the camera aperture.

20. A method as set forth in claim 19, including the step of focusing the real image from the borescope through the optical means by longitudinally translating a multi-element relay lens assembly within the adapter.

21. A method as set forth in claim 19, including the step of selecting a desired angular orientation between the borescope and adapter, and fixing the borescope and the adapter in the selected angular orientation during the step of coupling the borescope to the first end of the adapter.

22. A method as set forth in claim 21, including the step of selecting a desired angular orientation between the camera and adapter, and fixing the camera and the adapter in the selected angular orientation during the step of coupling the camera to the second end of the adapter.

23. A method as set forth in claim 19, including the step of inserting an optical filter between the borescope and the camera without uncoupling the adapter.

* * * * *

UNITED STATES PATENT AND TRADEMARK OFFICE
CERTIFICATE OF CORRECTION

PATENT NO. : 4,862,199

DATED : August 29, 1989

INVENTOR(S) : Mark Centkowski; Steven E. Manios, Sr.; and James Weaver

It is certified that error appears in the above-identified patent and that said Letters Patent is hereby corrected as shown below:

In column 4, line 27, insert the word --adapter;-- after "improved."

In column 7, line 25 insert between "invention." and "adapter":

--The adapter 10 is provided with a generally semi-circular filter slot 84 which is located within the adapter housing 50 between the relay lens assembly 48 and the camera coupling ring 66. This feature beneficially allows for the insertion of an auxiliary lens or filter 46 (see FIG. 5) between the optical scope 12 and the attached camera while the optical scope and camera 14 remain connected to the adapter 10. Previously, a photographer desiring to take special effects pictures using a coupled optical scope and camera arrangement would have to uncouple either the optical scope or the camera from the adapter so that a shutter attachment or the like, could be attached to provide special effects filters. In instances when the optical scope is an endoscope being used in surgery or during an examination, this uncoupling step is highly undesirable. The present invention eliminates this uncoupling step and provides for quick and easy insertion of an auxiliary lens or filter 46 into the filter slot 84 as needed. The filter slot can be configured in a variety of ways, however a generally semi-circular shape is preferred. Although illustrated with a filter slot capable of holding only one auxiliary lens or filter 46, the adapter 10 can be provided with a wider filter slot capable of holding multiple filters simultaneously, or it can be configured with more than one filter slot spaced within the adapter housing.

From the foregoing, it will be appreciated that a coupled optical scope 12 and camera 14 using the improved adapter 10 provides a higher degree of camera resolution because attachment

UNITED STATES PATENT AND TRADEMARK OFFICE
CERTIFICATE OF CORRECTION

PATENT NO. : 4,862,199   Page 2 of 2

DATED : August 29, 1989

INVENTOR(S) : Mark Centkowski; Steven E. Manios, Sr.; and James Weaver

It is certified that error appears in the above-identified patent and that said Letters Patent is hereby corrected as shown below:

is made with the optical scope's eyepiece optics 30, and the camera lens, removed. Further, the adapter 10 allows for the selective orientation of the optical scope 12 with respect to the camera 14, and permits insertion of an auxiliary lens or filter 46 while the optical scope and camera remain coupled to the adapter. Moreover, the--

Signed and Sealed this

Twenty-fifth Day of September, 1990

Attest:

HARRY F. MANBECK, JR.

*Attesting Officer*   *Commissioner of Patents and Trademarks*